(12) United States Patent
Shinmyo et al.

(10) Patent No.: US 6,573,429 B1
(45) Date of Patent: Jun. 3, 2003

(54) DNA FRAGMENT FOR STABLE EXPRESSION OF AN EXOGENOUS GENE IN A PLANT

(75) Inventors: Atsuhiko Shinmyo, Nara Pref. (JP); Kazuya Yoshida, Nara Pref. (JP); Ko Kato, Nara Pref. (JP); Shingo Nagaya, Nara Pref. (JP); Michio Shibata, Nara Pref. (JP); Ryutaro Aida, Nara Pref. (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/711,933

(22) Filed: Nov. 15, 2000

(51) Int. Cl.⁷ .............................. A01H 1/00; A01H 5/00; A01H 7/00; C07H 21/02; C12N 15/00; C12N 15/82
(52) U.S. Cl. .................... 800/287; 800/312; 800/317; 800/317.3; 800/317.2; 800/320.1; 800/320.2; 800/323.1; 435/320.1; 435/468; 536/24.1
(58) Field of Search ................... 800/298, 278, 800/279, 288, 287, 317, 317.2, 317.3, 320.1, 320.2, 312, 323.1; 435/468, 320.1; 536/24.1

(56) References Cited

PUBLICATIONS

Finnegan et al., Transgene Inactivation: Plants Fight Back!, Sep. 1994, Bio/Technology, vol. 12, pp. 883–887.*
Izawa et al., Plant bZIP Protein DNA Binding Specificity, 1993, J. Mol. Biol., vol. 230, pp. 1131–1144.*
Hao et al., Unique Mode of GCC Box Recognition by the DNA–binding Domain of Ethylene–responsive . . . , Oct. 9, 1998, The Journal of Biological Chemistry, vol. 273, No. 41, pp. 26857–26861.*
Eshed et al., Establishment of polarity in lateral organs of plants, 2001, Current Biology, vol. 11, pp. 1251–1260.*

* cited by examiner

Primary Examiner—Elizabeth F. McElwain
Assistant Examiner—Stuart F. Baum
(74) Attorney, Agent, or Firm—Burns, Doane, Swecker & Mathis, LLP

(57) ABSTRACT

A method useful for stable expression of an exogenous gene, introduced into a plant, is provided. By introducing an exogenous gene and 5' upstream sequence of tobacco dehydogenase concurrently, stable expression of the exogenous gene introduced into a plant can be achieved.

9 Claims, 6 Drawing Sheets

(2 of 6 Drawing Sheet(s) Filed in Color)

SEQUENCE LISTING

<160> NUMBER OF SEQ ID NOS: 1

<210> SEQ ID NO 1
<211> LENGTH: 214
<212> TYPE: DNA
<213> ORGANISM: Nicotiana tabacum

<400> SEQUENCE: 1

```
gggtcaaaac atcgttaggt ttaataaatc aaatcgattt ttctcttgaa atattaccac      60 caccttttc ttattactcg acaaaaactc aaacagtaac acaaaacaaa cagccaaaaa     120
ccggtttcga aaacccagcg accaaaacat ggaaatggtt ttactttggc ctgttgtatt     180
caacttttcg atttcacgat tctatatttt cagg                                 214
```

DNA FRAGMENT FOR STABLE EXPRESSION OF AN EXOGENOUS GENE IN A PLANT

RELATED APPLICATIONS

This application claims priority under 35 U.S.C. §§119 and 365 to Application No. 11-329,400 filed in Japan on Nov. 19, 1999.

BACKGROUND OF THE INVENTION

1. Field of the Invention

This invention relates to a DNA fragment for stable expression of an exogenous gene in a plant, a method to introduce an exogenous gene for stable expression of an exogenous gene, and a transgenic plant for stable expression of an exogenous gene.

2. Description of Related Arts

Many kinds of transgenic plants, wherein exogenous genes are introduced, have been produced to render various characteristic to the plants. In the production of such transgenic plants, the diversity of gene expression observed among individual transgenic plants makes some problems. It is considered that such diversity is caused by the introduced position of a gene in a chromosome. When an exogenous gene is introduced into active chromatin region, high expression of the exogenous gene would be obtained. On the contrary, when an exogenous gene is introduced into inert chromatin region, sufficient expression of the gene would not be obtained (Galli, Current opinion in plant technology (1998) 1:166–172, Matzke et al., Current opinion in plant technology (1998) 1:142–148). Such effect described above is called "position effect". Because of the position effect, an exogenous gene, introduced into a plant, exhibits absolute failure of expression, only weak expression or suppression of expression depending on plant growth or surrounding environment. This phenomenon deserves a barrier on commercialization of a transgenic plant and establishment of a method to stabilize expression of an introduced gene have been demanded.

Recently, some transformants, wherein genes of various kinds are introduced, revealed constant expression of the gene independent of its introduced position in the chromosome. The factors concerning such phenomenon are classified into three cases. These are, insulator and MAR (matrix attachment region). Moreover, involvement of such factors on constant expression is suggested. These three factors function as boundaries in a chromosome and blockade effects of near-existing chromatin, though the mechanisms of action of these factors differ with each other.

MAR, described above, is utilized for stable expression of an exogenous gene introduced into a plant by inhibiting the position effect. MAR contains an adenine, thymine (AT) rich sequence and a topoisomerase II recognition sequence. Moreover, MAR is a functional region exhibiting nuclear-matrix binding activity under in virto condition. MAR is considered to exist more than every 10–100 kb in a chromosome, and the chromosome binds to nuclear matrix through these regions to form conformation of the chromosome. MAR is indispensable for compaction of chromosome in a limited space of nucleus. The knowledge indicating that the MAR might be involved in the regulation of gene expression is accumulating in recent researches.

Moreover, it is speculated that, a chromatin loop is formed among plural MAR's which assures independence of gene expression in the loop. The effect of MAR, when utilized for stabilization of gene expression, was not consistent among experiments and stable expression of introduced gene was not achieved in many cases. This result might be caused by the following phenomenons.

(1) Plenty of MAR's might operate to increase expression of introduced gene.

(2) When plural copies are introduced, expression of introduced gene might be suppressed by other effects than the position effect, for example, specific methylation of DNA.

Therefore, MAR may not necessarily function as a boundary on the chromosome (Galli, Current opinion in plant technology (1998)1:166–172, Matzke et al., Current opinion in plant technology (1998)1:142–148), resulting in failure of generalization of the technique using MAR.

On the other hand, the insulator described above is also utilized to inhibit the position effect. Here, an enhancer is a DNA sequence that enhances transcriptional activity of a promoter. On the contrary, a silencer is a DNA sequence that attenuates or vanishes the transcriptional activity of a promoter. In detail, two kinds of mechanisms are reported concerning occurrence of silencer function. These are; the DNA sequence of a silencer or conformational structure of a chromosome (chromatin structure) would be involved in inhibition of transcriptional activity of the promoter. An insulator is defined as a functional region (DNA fragment) which blockades such interference effect caused by adjoining genes such as an enhancer or a silencer. In a higher eukaryotic plant, an enhancer and a silencer might cause an effect on transcriptional activity of not only a certain promoter, but also plural promoters. It should be noted that an enhancer or a promoter can cause its transcriptional activity, even to a gene localized at a distance of several bps. Therefore, plural elements might cause effects randomly in a chromosome. This phenomenon might work to render diversity on gene expression. On the other hand, a mechanism to restrict the enhancer function or the silencer function might be necessary for precise regulation of gene expression. At present, it is speculated that an insulator might operate to restrict these functions.

Hitherto, insulators have been identified from various organisms, for example, Drosophila. The examples of insulators identified are, gypsy insulator, scs-scs' insulator and Fab-7 insulator originated from Drosophila, beta globin insulator originated from chicken, apoB insulator originated from chicken and human. The identification of proteins involved in insulator function have been performed recently, in particular, the analysis on gypsy insulator, scs-scs' insulator is advanced. Among these researches, it is reported that, beta globin insulator originated from chicken affects to stabilization on gene expression regardless of the origin of the gene. Moreover, the inventors have showed stable expression of an exogenous gene achieved by ligating an insulator isolated from sea urchin arylsulfatase (Japanese patent application No. 11-253174). On the basis of knowledge described above, this invention was performed with the aim to obtain a novel gene which enables stable expression of an exogenous gene introduced.

SUMMARY OF THE INVENTION

This inventors isolated some promoters, which enables high extent of expression, from tobacco cultured cell (*Nicotiana tabacum.* BY-2). Each of the DNA fragment of the promoter thus obtained was ligated to GUS reporter gene, then introduced into tobacco cultured cell. Moreover, GUS activity of each dependent transformed clone was investigated. As the result, the expression of a promoter, derived from tobacco alcohol dehydrogenase (NtADH) gene, showed only few diversity among plural clones.

From knowledge described above, the inventors have searched a nucleotide sequence, which is responsible for stable expression of a gene, in promoter region of NtADH. The region capable of stable expression a gene according to this invention, designated to ADH200, was thus obtained. The detailed characteristic of ADH200 will be described below. ADH200 is expected to be very useful as a novel technique to stabilize expression of an exogenous gene introduced into a plant and contribute to progression of plant bio-industry.

This invention provides a novel DNA fragment useful for stable expression of an exogenous gene introduced into a plant. The DNA fragment according to this invention is consisted of a base sequence derived from promoter region of tobacco alcohol dehydrogenase (NtADH), corresponding to the region from TATA box to 214 bp upstream of TATA box. The inventors have found that said base sequence stabilizes expression of a gene and designated the base sequence as ADH200. In this specification, the wording "stabilization of expression of a gene" indicates that the ratio of individuals, exhibiting no activity or extremely low activity of an exogenous gene introduced, is significantly decreased. The base sequence of ADH200 of this invention is specified by SEQ ID No. 1 in a sequence list. Moreover, a DNA fragment consisting of a base sequence with high homology to said ADH200, a part of which is deleted or substituted by another sequence, or to which another sequence is added, is in the range of this invention, so far as the DNA fragment is capable of stabilizing expression of an exogenous gene.

The DNA fragment of this invention includes a DNA fragment consisting of a base sequence that hybridizes with the base sequence referred to as SEQ ID No. 1 in the sequence list under stringent condition.

Moreover, the ADH200 DNA fragment of this invention includes a DNA fragment having a base sequence at least 70% of sequence homology with the base sequence referred to as SEQ ID No. 1 in the sequence list, as far as retaining biochemical characteristic as ADH200 DNA fragment. In preferred form, the base sequence of this invention have more than 80% of sequence homology with the base sequence referred to as SEQ ID No. 1 in the sequence list. In more preferred form, the base sequence of this invention have more than 90% of sequence homology with the base sequence referred to as SEQ ID No. 1 in the sequence list.

A vector comprising a fusion gene, the fusion gene consisting of DNA fragment of ADH200, an exogenous gene to be introduced and an exogenous promoter locating between said DNA fragment of ADH200 and said exogenous gene to regulate expression of said exogenous gene, is also in the range of this invention. That is, a vector, containing a fusion gene, the fusion gene consisting of an exogenous promoter located 5' upstream of an exogenous gene to be introduced and said ADH200 DNA fragment ligated further 5' upstream of said exogenous promoter, is also in the range of this invention. Moreover, a vector, containing a fusion gene, the fusion gene consisting of an exogenous promoter located 3' downstream of an exogenous gene to be introduced and said ADH200 DNA fragment ligated further 3' downstream of said exogenous promoter, is also in the range of this invention. In this specification, an exogenous promoter means that the origin of the promoter is different from host plant, to which an exogenous gene to be introduced. As described in the following embodiment, the ADH200 DNA fragment stabilizes expression of an exogenous gene by stabilizing expression of an exogenous promoter. Therefore, ADH200 gene can stabilize expression of an exogenous gene introduced, even if ADH200 is located outside of the promoter, which is the most prominent feature of this invention.

As shown in the embodiment, the expression of an exogenous gene can be stabilized by introducing said vector, comprising said ADH200 DNA fragment, an exogenous gene and an exogenous promoter, into a plant. A method to introduce an exogenous gene comprising such process is also in the range of this invention. Moreover, a transgenic plant with an exogenous gene introduced by the method described above to achieve stable expression of the exogenous gene, is also in the range of this invention. As described in the following embodiment, expression of an exogenous gene is stabilized using ADH200 DNA fragment of this invention. That is, the number of individuals, with an exogenous gene introduced failed to express its activity or individuals with the extent of expression of an exogenous gene was very low, decreased significantly.

By using the method of this invention, stable expression of various exogenous gene can be achieved. Theoretically, any gene can be adopted as an exogenous gene to be introduced in a host plant. The examples of exogenous genes preferred to be introduced in a host plant are as described below. These are disease or insect injury resistance genes such as peroxidase gene or chitinase gene, genes for ectoine biosynthesis such as L-2,4-diaminobutyric acid acetyltransgerase, L-2,4-diaminobutyric acid transaminase and ectoine synthetase, genes for betaine biosynthesis such as choline oxidase and second metabolite producing gene such as fatty acid biosynthesis. Moreover, an exogenous gene can be introduced into various host plants according to the method of this invention, theoretically, any plant can be adopted as a host plant to be introduced an exogenous gene. The examples of plants preferred to be adopted as a host plant are as described below. These are benetificial cultivated plants such as tobacco, Arabidopsis or petunia, crops such as rice, maize, potato, sweet potato, soybean, strawberry or eggplant and trees such as blue gum or white poplar.

The above description and following example are intended to only illustrate this invention, not to be intended to limit the range of this invention.

BRIEF DESCRIPTION OF THE DRAWINGS

The patent or application file contains at least one drawing executed in color. Copies of this patent or patent application publication with a color drawing will be provided by the Office upon request and payment of the necessary fee.

DETAILED DESCRIPTION OF THE EMBODIMENTS

EXAMPLES (Constitution of Plasmid)

Figure 1:
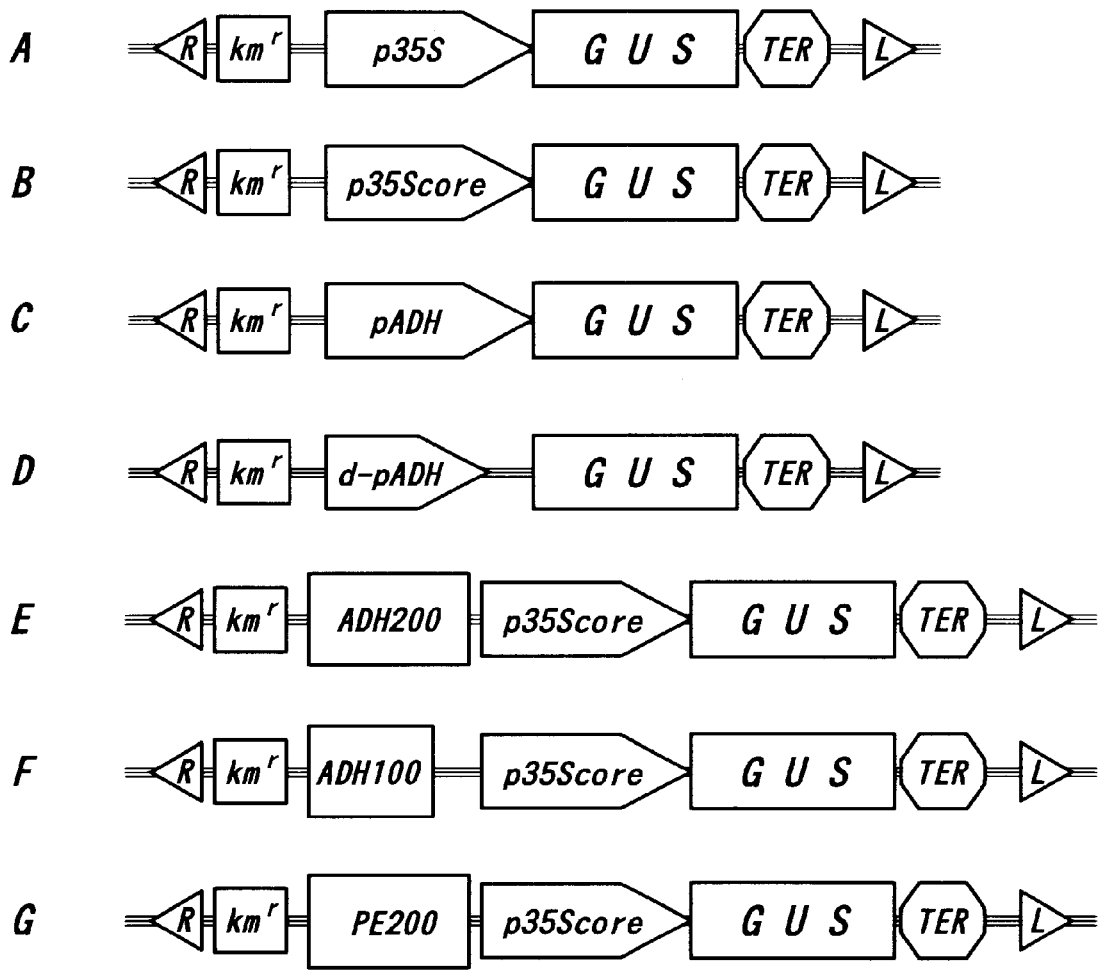
FIG. 1 is a schematic view showing structure of T-DNA of binary plasmid constructed.

Fusion genes used in the experiments of the present invention are shown in FIG. 1.

(A) 35S-GUS: β-Glucronidase gene (GUS) derived from E.coli was ligated to downstream of promoter of cauliflower mosaic virus 35S (CaMV35S) RNA gene.

(B) 35S core-GUS: GUS gene was ligated to downstream of CaMV35S core promoter (core sequence of 90 bp).

(C) pADH-GUS: GUS gene was ligated to tobacco alcohol dehydrogenase (NtADH) promoter.

(D) d-pADH-GUS: GUS gene was ligated to DNA fragment of NtADH promoter corresponding to the region from TATA box to 214 bp upstream of TATA box.

(E) ADH200-core-GUS: ADH200 was conjugated to 5' upstream of CaMV35S core promoter (90 bp)-GUS fusion gene.

(F) ADH100-core-GUS: 110 bp (ADH100) of DNA fragment, corresponding to 5' region of ADH200, was ligated to 5' upstream of CaMV35S core promoter GUS fusion gene.

(G) PE200-core-GUS: About 200 bp (PE200: literature for reference: Shinmyo et al., Biotech, Bioeng., 1998, 58: 329–332) of DNA fragment derived from pectin esterase gene, corresponding to the 5' upstream region from TATA box to 200 bp upstream of TATA box, was ligated to CaMV35S core promoter GUS fusion gene (negative control).

As well, in the structures of fusion genes shown in FIG. 1, the symbols indicate the following genes, respectively.

R: Right border sequence of T-DNA
L: Left border sequence of T-DNA
Km': Kanamycin resistant gene
TER: Terminator of nos gene (Introduction into Tobacco Culture Cell)

The binary plasmids (corresponding to A–G mentioned above) were introduced into chromosomes of tobacco culture cell (BY2) respectively, by the Agrobacterium infection method, as described in Gynheung et al. (Gynheung et al., Plant. Physiol. (1985) 79:568–570). The putative transformed cells, in which the targeted gene was assumed to be introduced, were selected according to phenotype expression of Kanamycin resistance.

(Measurement of Beta Glucronidase Activity)

Independent transformants, namely independent 50 clones, of each genes described above (A–F) were obtained, and beta glucuronidase activity (GUS activity) of the clones was measured. As well, concerning the negative control (G), independent 25 clones were obtained. One mM of 5-bromo-4-chloro-3-β-D-glucuronic acid was added as a substrate and the mixture was reacted at 37° C. for 12 hours. As the result of present reaction, the clones exhibiting GUS activity were stained to blue color. The patterns of staining obtained from GUS activity experiments are shown in FIG. 2 to FIG. 8, and digitized results of GUS activity obtained from FIG. 2 to FIG. 8 are shown in Table 1. In Table 1, potency of the GUS activity is shown by following symbols.

++: high GUS activity +: low GUS activity –: detection limit or less.

The numeric values in Table 1 indicate the numbers of transformants exhibiting GUS activities at the extent designated by above symbols.

TABLE 1

List of expression manner of various fusion genes

| Introduced fusion gene | ++ | + | – | Total |
| --- | --- | --- | --- | --- |
| A. p35S-GUS | 22 | 14 | 14 | 50 |
| B. pNtADH(2.5 kb)-GUS | 50 | 0 | 0 | 50 |
| C. pNtADH(0.3 kb)-GUS | 50 | 0 | 0 | 50 |
| D. p35S core-GUS | 12 | 24 | 14 | 50 |
| E. ADH200-p35S core-GUS | 50 | 0 | 0 | 50 |
| F. ADH100-p35S core-GUS | 44 | 4 | 2 | 50 |

(Stabilization of Gene Expression by NtADH Promoter)

Figure 2:
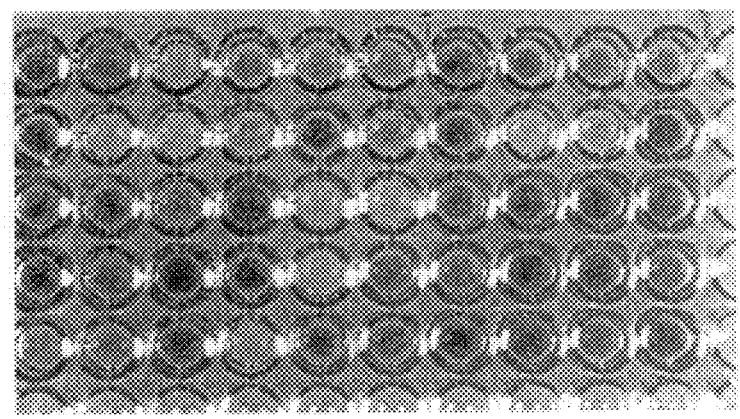
FIG. 2 is a photograph showing GUS activity staining of BY2 cell with CaMV35S-GUS introduced.
Figure 4:
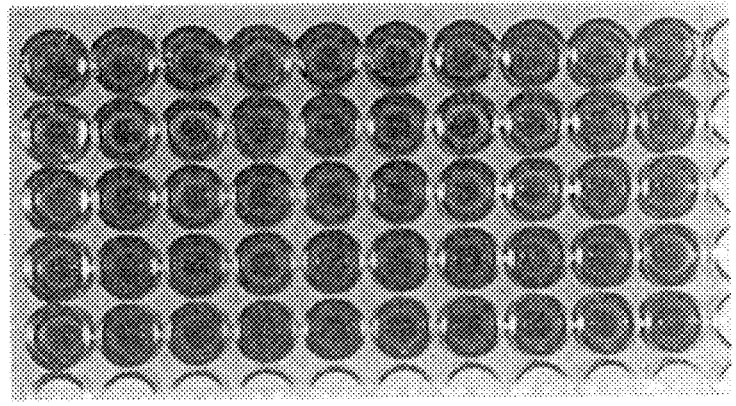
FIG. 4 is a photograph showing GUS activity staining of BY2 cell with pADH-GUS introduced.

Using GUS activities as an index, stabilization of an introduced gene was further investigated. In 35S-GUS fusion gene (FIG. 1A), about 30% of transformants failed to be stained (FIG. 2, Table 1A). Concerning transformants exhibiting no GUS activity, incorporation of the introduced gene into chromosome was confirmed using PCR method. On the contrary, in the NtADH promoter GUS fusion gene (FIG. 1C), high extent of GUS activity was detected among overall clones examined (FIG. 4, Table 1B). In the 35S-GUS fusion gene, diversity of gene expression was confirmed by experiments repeated several times in the same manner. This result indicates that the NtADH promoter bears a mechanism that enables stabilization of expression of a gene, introduced into chromosome of a plant cell.

(Deletion Analysis of Promoter)

Figure 5:
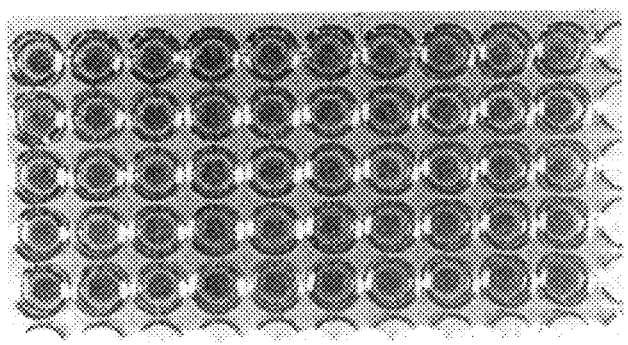
FIG. 5 is a photograph showing GUS activity staining of BY2 cell with d-pADH-GUS introduced.
Figure 9:
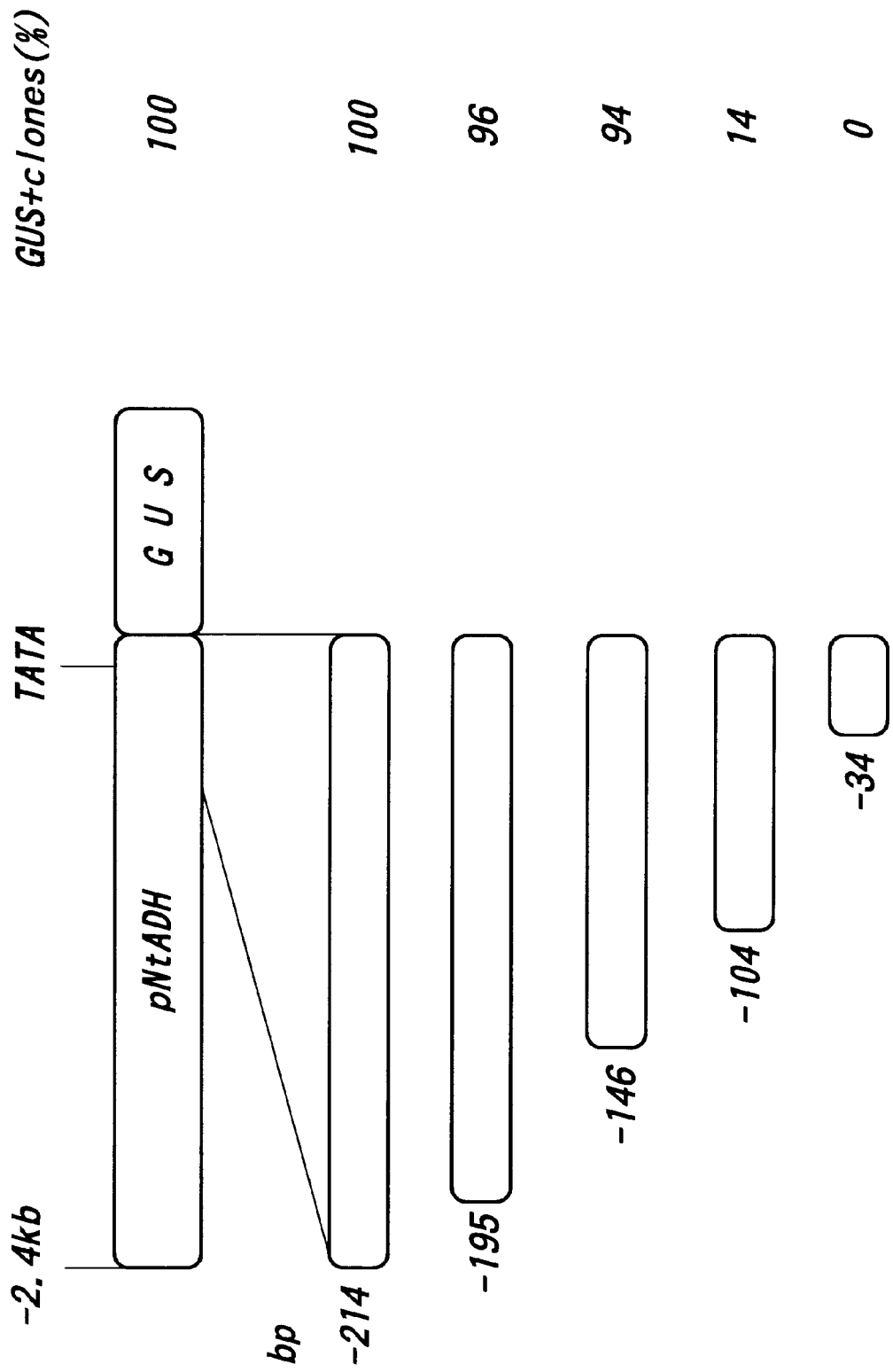
FIG. 9 is a schematic view showing structure of each ADH promoter with 5' side is deleted step-wisely, and percentage of GUS positive clone of each promoter.

Thus, the region responsible for stabilization of gene expression was identified, by deletion analysis of the NtADH promoter. As shown in FIG. 1D, fusion gene consisting of GUS gene and DNA fragment of NtADH promoter, corresponding to the region from TATA box to 214 bp upstream of TATA box (FIG. 1D), was constructed. As the result, BY2 cells, to which the fusion gene described above (FIG. 1D) was introduced, all clones exhibited GUS staining (FIG. 5, Table 1E). Moreover, further analysis for detailed identification of the region responsible for the stabilization, same analysis was performed on DNA fragments in which the sequence described above was deleted, at about 20 bps as an unit, from the 5' upstream in the stepwise manner (FIG. 9). That is, GUS gene was ligated to DNA fragments, corresponding to the region from TATA box to 214 bp, 195 bp, 146 bp, 104 bp, and 34 bp upstream of TATA box respectively, to produce fusion genes and the fusion genes were introduced into BY2 cell. Then the percentage of clones (GUS+%), exhibiting high GUS activity in the independent 50 clones, was designated in FIG. 9. As the result, the diversity of gene expression was observed on fusion gene, in which GUS gene was ligated to DNA fragment corresponding to the region from TATA box to 195 bp upstream of TATA box, and the ratio of clones exhibiting high GUS activity was 96%. When GUS gene was ligated to a DNA fragment with higher deletion, the DNA fragments corresponding to the region from TATA box to 146 bp, 104 bp or 34 bp upstream of TATA box, the ratio of clones capable of exhibiting GUS activity further decreased.

Figure 10:
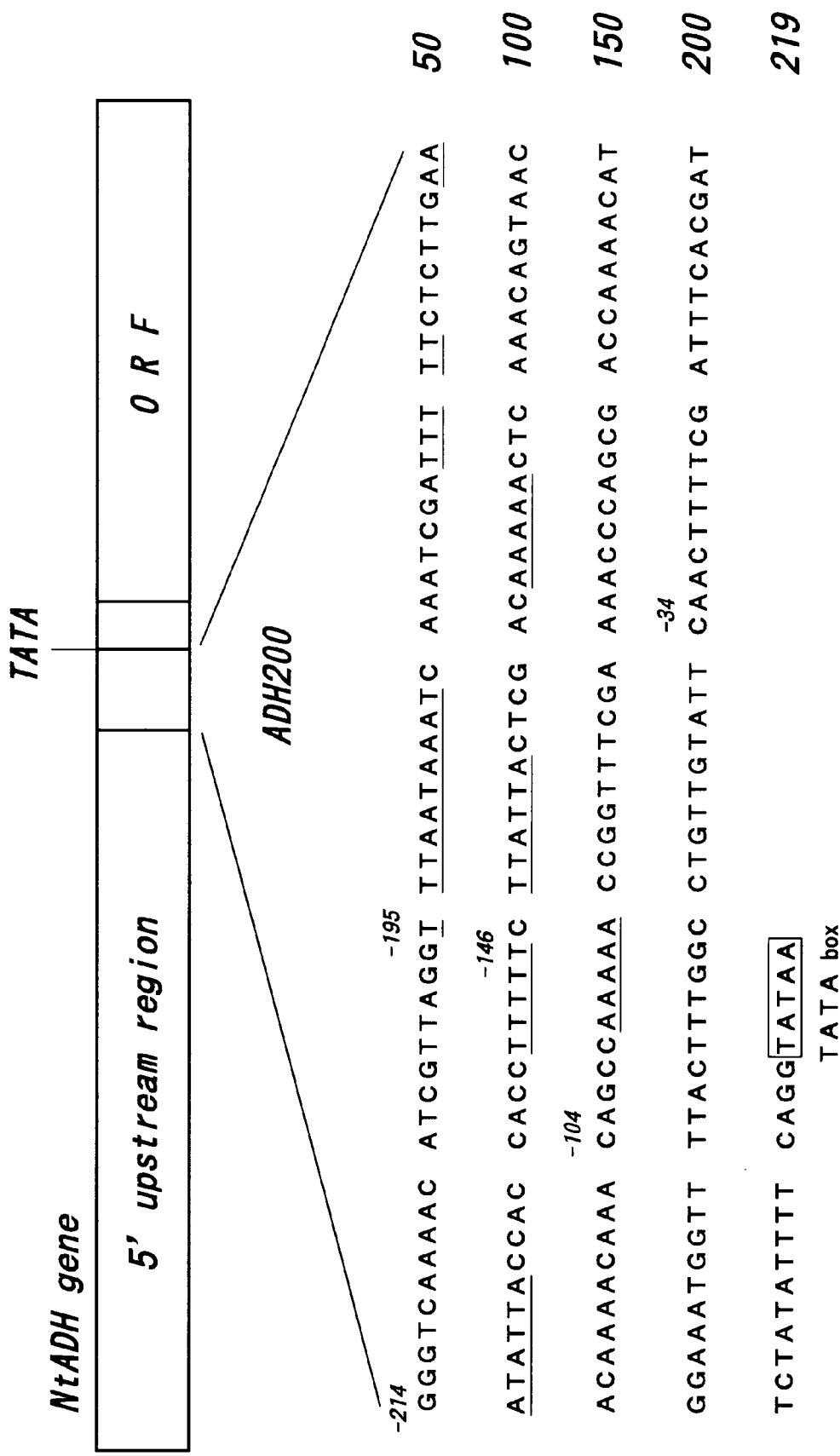
FIG. 10 is a schematic view showing structure of ADH200 region in NtADH gene and base sequence of ADH200.

From the results mentioned above, the minimum portion of DNA fragment, sufficient to function for stabilization of gene expression, was identified. That is, the DNA fragment of NTADH gene, corresponding to the region from immediately upstream of TATA box to 214 bp 5' upstream of TATA box. Said DNA fragment is the ADH200 of the present invention. The position corresponding to the ADH200 in the NtADH promoter gene and the base sequence are shown in FIG. 10. As well, in the base sequence of FIG. 10, TATA box existing at the 3' terminal is not included in the ADH200 DNA fragment. In FIG. 10, TATA indicates TATA box and ORF indicates open reading frame, the region translated to corresponding protein. As the characteristic feature of the base sequence of the ADH200, some nucleotide sequences of 4–5 bases, comprising continued adenine (A) or thymine (T), are observed repeatedly. It has been suggested that a region containing such sequence generally functions to render a folded structure to a DNA. It is considered that such characteristics in the base sequence contribute for stabilization of gene expression.

(Stabilization on Expression of Heterogeneous Promoter by ADH200)

Figure 3:
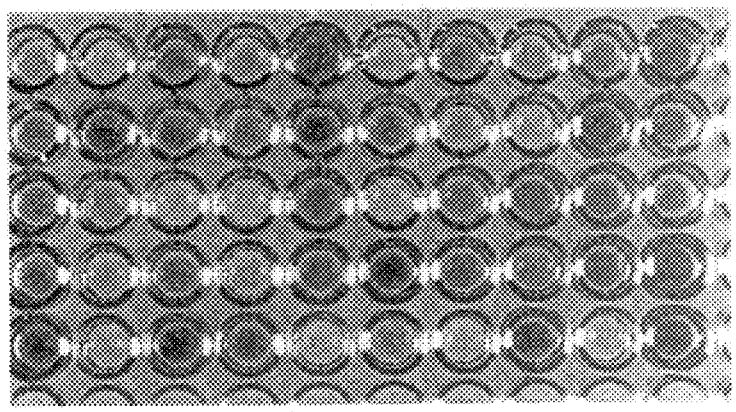
FIG. 3 is a photograph showing GUS activity staining of BY2 cell with CaMV35Score-GUS introduced.
Figure 6:
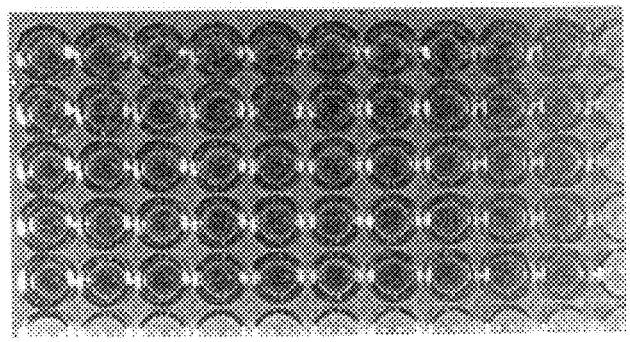
FIG. 6 is a photograph showing GUS activity staining of BY2 cell with ADH200-core-GUS introduced.
Figure 7:
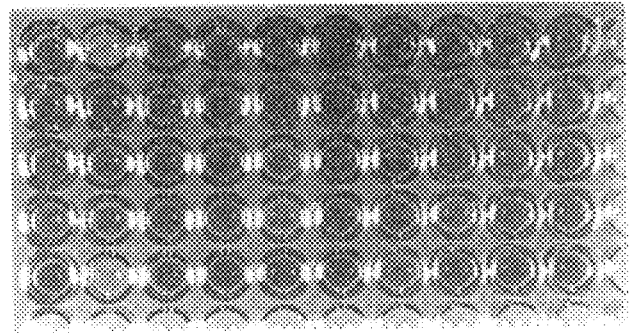
FIG. 7 is a photograph showing GUS activity staining of BY2 cell with ADH100-core-GUS introduced.

Next, the potency of ADH200 to stabilize expression of a heterogeneous promoter was investigated. The ADH200 was ligated to 5' upstream region of cauliflower mosaic virus (CaMV) 35S core promoter (90 bp)-GUS fusion gene (FIG. 1E). It was introduced into BY2 cell and the extent of expression of the CaMV promoter was evaluated, using GUS activity as an index. The diversity in gene expression was observed on the transformant, to which CaMV35S core promoter (90 bp)-GUS fusion gene (FIG. 1B) was introduced (FIG. 3). On the other hand, concerning ADH200-CaMV35S core promoter GUS fusion gene, high GUS activity was observed on all clones examined (FIG. 6). A DNA fragment of 110 bp (ADH100), corresponding to 110 bp of 5' region of ADH200, was ligated to 5' upstream of the CaMV35S core promoter GUS fusion gene (FIG. 1F). As the result, clones exhibiting low GUS activity were observed and the DNA fragment failed to stabilize gene expression (FIG. 7, Table 1F).

Figure 8:
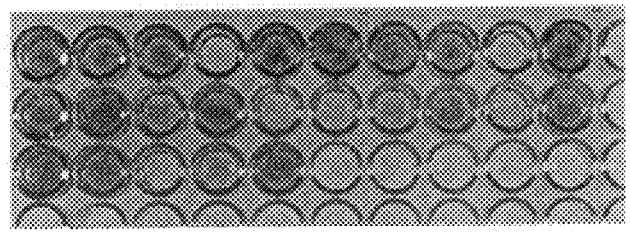
FIG. 8 is a photograph showing GUS activity staining of BY2 cell with PE200-core-GUS introduced.

Moreover, in PE200-CaMV35S core promoter GUS fusion gene, in which PE200 was ligated as negative control (FIG. 1G), clones exhibiting low GUS activity were observed and diversity of gene expression was recognized (FIG. 8). In FIG. 8, GUS activity of 6 samples, among 25 samples, revealed to be lower than the detection limit. This result indicates that expression of a promoter incorporated into a chromosome can be stabilized by ligating DNA fragment of ADH200 to 5' upstream region.

Figure 11:
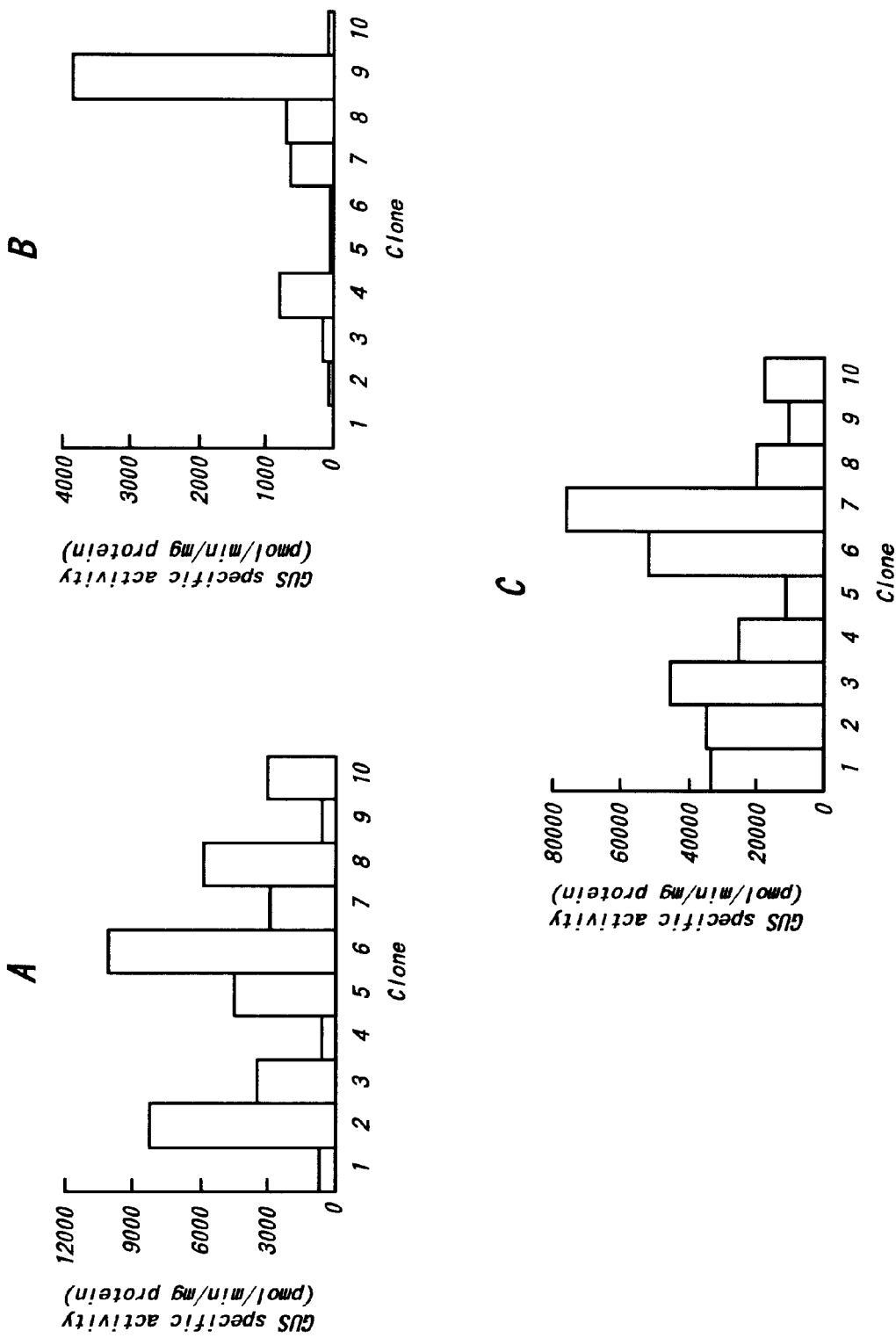
FIG. 11 is a graph showing GUS activity of BY2 cell, in which each DNA constructed were introduced.

For further investigation on stabilization of promoter function by ligating ADH200 as described above, quantitative measurement of GUS activity on BY2 clones, bearing fusion genes of A, B or E shown in FIG. 1, was performed (FIG. 11). That is, 10 clones were selected from each fusion gene randomly, and GUS activity of the selected clones was measured. In FIG. 11, A shows the result of GUS activity measured on clones with 35S-GUS (FIG. 1A) introduced, B shows that measured on clones with 35S core-GUS (FIG. 1B) introduced and C shows that measured on clones with ADH200-core-GUS (FIG. 1E) introduced, respectively. In A, B and C of FIG. 11, 10 clones were selected randomly from 50 clones of FIG. 2, FIG. 3 and FIG. 6, respectively. Then enzymatic reaction using 4-methyl-unberypheryl glucuronide was performed using crude extracts derived from cells of 10 clones selected above, as samples of GUS activity measurement. In FIG. 11, the amount of reaction product (pmol) per unit time and unit protein weight was designated as specific activity.

As the result, in 35S promoter and 35S core promoter, clones exhibiting GUS activity of lower than detection level or GUS activity of extremely low level were observed. That is, the GUS activity of 3 clones of 35S-GUS was less than 1000 pmol/min/mg (FIG. 11A) and that of 4 clones of 35S core-GUS was less than 100 pmol/min/mg (FIG. 11B). On the contrary, in the CaMV35S promoter with ADH200 ligated to 5' upstream (ADH200-core-GUS), all the clones exhibited GUS activity of higher than 10000 pmol/min/mg (FIG. 11C). From the results described above, by ligating ADH200, clones failed to exhibit GUS activity or clones exhibiting extremely low activity disappeared, indicating that, stabilization of gene expression was achieved.

According to this invention, suppression of diversity of gene expression, caused by failure of expression of a gene introduced, was achieved by ligating the ADH200 gene of the present invention to a gene to be introduced. Therefore, stable expression of a gene was realized to produce a transformed plant. The present technique is expected to be valuable in the molecular breeding of a beneficial plant or the production of a beneficial compound in a plant, which was achieved by production of a transformed plant. In other words, expression of an introduced gene can be controlled precisely by ligating ADH200, which was achieved by blockage of effect caused by surrounding transcriptional environment in chromosome. Moreover, this invention is expected to contribute to and increase the safety of a transgenic plant with an exogenous gene expressed.

What is claimed is:

1. A DNA fragment comprising nucleotides from 1–214 in SEQ ID NO:1.

2. A vector comprising a fusion gene, said fusion gene comprising said DNA fragment according to claim 1, an exogenous gene to be introduced into a plant and an exogenous promoter located between said DNA fragment and said exogenous gene, wherein said exogenous promoter is from an organism other than said plant, wherein said fusion gene is expressed and the expression of an exogenous gene is stabilized.

3. The vector according to claim 2, wherein said DNA fragment enables stable expression of said exogenous gene in said plant.

4. The vector according to claim 2, wherein said exogenous gene is selected from the group consisting of peroxidase gene, chitinase gene, L-2,4-diaminobutyric acid acetyltransgerase gene, L-2,4-diaminobutyric acid transaminase gene, ectoine synthetase gene, betaine synthetase gene, choline oxidase gene and fatty acid synthetase gene.

5. The vector according to claim 2, wherein said plant is selected from the group consisting of tobacco, Arabidopsis, petunia, rice, maize, potato, sweet potato, soybean, strawberry, eggplant, blue gum and white poplar.

6. A method for introducing an exogenous gene into a plant, the method comprising the step of introducing the vector according to claim 2 into a plant, wherein said DNA fragment enables stable expression of said exogenous gene in said plant.

7. The method according to claim 6, wherein said exogenous gene is selected from the group consisting of peroxidase gene, chitinase gene, genes, L-2,4-diaminobutyric acid acetyltransgerase gene, L-2,4-diaminobutyric acid transaminase gene, ectoine synthetase gene, betaine synthetase gene, choline oxidase gene and fatty acid synthetase gene.

8. The method according to claim 6, wherein said plant is selected from the group consisting of tobacco, Arabidopsis, petunia, rice, maize, potato, sweet potato, soybean, strawberry, eggplant, blue gum and white poplar.

9. A method to stabilize expression of an exogenous gene, the method comprising the step of introducing the vector according to claim 2 into a plant, wherein said fusion gene is expressed and the expression of an exogenous gene is stabilized.

* * * * *